US009079280B2

(12) United States Patent
Lange et al.

(10) Patent No.: US 9,079,280 B2
(45) Date of Patent: Jul. 14, 2015

(54) APPARATUS AND METHOD FOR MONITORING A TOOL MACHINE

(75) Inventors: Dirk Lange, Lueneburg (DE); Volker Redecker, Bispingen (DE); Heribert Josef Messing, Schoeppingen (DE)

(73) Assignee: ARTIS GmbH, Egestorf (DE)

( * ) Notice: Subject to any disclaimer, the term of this patent is extended or adjusted under 35 U.S.C. 154(b) by 747 days.

(21) Appl. No.: 13/347,177

(22) Filed: Jan. 10, 2012

(65) Prior Publication Data

US 2012/0182029 A1    Jul. 19, 2012

(30) Foreign Application Priority Data

Jan. 14, 2011  (EP) ..................................... 11150997

(51) Int. Cl.
| | | |
|---|---|---|
| G01R 27/08 | (2006.01) | |
| G01R 31/08 | (2006.01) | |
| B23Q 17/09 | (2006.01) | |
| G01R 27/00 | (2006.01) | |
| G01N 3/56 | (2006.01) | |

(52) U.S. Cl.
CPC ................ B23Q 17/09 (2013.01); G01R 27/00 (2013.01); G01N 3/56 (2013.01); G05B 2219/37405 (2013.01)

(58) Field of Classification Search
CPC .................. G01R 27/00; G01R 27/02; G05B 2219/37405; G01N 3/56; B23Q 17/09
USPC ................................................... 324/525, 691
See application file for complete search history.

(56) References Cited

U.S. PATENT DOCUMENTS

| | | | | |
|---|---|---|---|---|
| 3,728,621 | A * | 4/1973 | Frost-Smith et al. | 324/699 |
| 4,326,257 | A * | 4/1982 | Sata et al. | 700/175 |
| 4,786,220 | A | 11/1988 | Fildes et al. | |
| 5,030,920 | A * | 7/1991 | Nakamura | 324/721 |
| 2002/0197122 | A1 * | 12/2002 | Mizutani et al. | 409/132 |

FOREIGN PATENT DOCUMENTS

| | | |
|---|---|---|
| EP | 2165203 | 3/2010 |
| EP | 2165803 A1 | 3/2010 |
| WO | 2006128892 | 12/2006 |

* cited by examiner

*Primary Examiner* — Amy He
(74) *Attorney, Agent, or Firm* — Meyertons Hood Kivlin Kowert & Goetzel, P.C.; Jeffrey C. Hood (57) ABSTRACT

The invention refers to an apparatus for monitoring the operation of an electrically conductive tool (120) of a machine tool (100, 400) having at least one electrically conductive spindle (110) for holding the tool (120) and a detector (140, 545, 645) which determines an electrical resistance (190, 290, 390) between the spindle (110) and the electrically conductive work piece (130) to be processed, and wherein the spindle (110) is electrically isolated from the machine tool (100, 400) and/or the apparatus is adapted to electrically isolate the work piece (130) to be processed from the machine tool (100, 400).

15 Claims, 9 Drawing Sheets

APPARATUS AND METHOD FOR MONITORING A TOOL MACHINE

PRIORITY CLAIM

This application claims benefit of priority of European application no. EP 11150997.2 titled "Vorrichtung and Verfahren zum Überwachen einer Werkzeugmaschine", filed Jan. 14, 2011, whose inventors are Dirk Lange, Volker Redecker, and Heribert Josef Messing and which is hereby incorporated by reference in its entirety as though fully and completely set forth herein.

1. TECHNICAL FIELD

The present invention refers to an apparatus and a method for monitoring a machine tool.

2. PRIOR ART

Nowadays high requirements are put on the profitability and the productivity of production plants. On the other hand, the produced work pieces have to have a high quality. These conflicting objectives can only be achieved with a high level of automation. Here a highly automated operation of a machine tool requires the utilization of data of various sensor systems in order to efficiently control the machine, and thus monitoring it.

The condition of the tool, which is used for the processing of a work piece, has a significant influence on the quality of the work piece to be produced. In automated production facilities a broken tool or a missing tool leads to high scrap rates when it not recognized in time. In the worse-case, defective work pieces or components are built into end products which can lead to high damages on the customer side.

The discussed problem also occurs if incorrect work pieces are not recognized or not recognized in time, and are thus processed by the production line. These work pieces have to be rejected at the end of the processing or are erroneously built into an end product. Thus, it is very important to recognize such sources of error in time and to remove them.

At the moment, there are already a number of systems and devices for monitoring the tool. On the one hand, these systems are based on a direct or indirect measurement of the power used during the machining. The patent specification DE 247 420 A1 describes an example for a direct power measurement.

For example, the published patent application DE 29 06 892 explains that for example piezoelectric oxides can be attached on the tool for an indirect measurement of the torque for monitoring the tool. The patent application DE 10 2006 834 and the published patent application DE 10 2004 051 145 A1 of the applicant describes how signals can be wirelessly transmitted to a stationary receiving unit from sensors arranged on the spindle of a machine tool.

The approach via a direct measurement is already often used in the field; however, it requires a minimum machining power which exceeds the noise level of the respective measurement signal (for example the effective power). However, this requirement is often not fulfilled for small tool diameters (for example for tools having a diameter <1 mm) which are particularly prone to breakages. The indirect measurement methods are complex, and it is often difficult to subsequently integrate them into already existing systems which significantly hampers their application under conditions of production.

Furthermore, there exists a variety of methods to measure the tool before or after its application. For example, the published application DE 1 033 991 discloses an inductive method to determine the length of a drill after its application. This method indeed determines whether the length of the drill is essentially the same before and after the processing. However, this method cannot be used to determine whether the correct drill is used, or whether there exists at all a work piece.

Due to a high degree of dirt, optical methods for determining the tool geometry can often be used in a limited way in an environment of machine tools. The application of tactile methods can lead to measurement uncertainties which are caused by coolants and/or chips. Moreover, the touching or scanning of tools can lead to the destruction of very small tool. In addition, the insertion of such monitoring systems in already existing systems requires a significant integration effort.

It is a general handicap of all pre and/or post process measurements that they require measurement times in which the machine is not available for the processing of work pieces. This drawback often prevents an economic application of these methods.

The present invention is therefore based on the problem to provide a simple, robust and cost-effectively useable apparatus as well as a respective method with which the tool of a machine tool and the respective work piece can be simply and reliably be monitored.

3. SUMMARY OF THE INVENTION

According to a first aspect of the invention this problem is solved by an apparatus according to claim 1. In one embodiment an apparatus for monitoring the operation of an electrically conducting tool of a machine tool comprises at least one electrically conducting spindle for holding the tool, a detector which measures the electrical resistance between the spindle and an electrically conducting work piece to be processed, wherein the spindle is electrically isolated from the machine tool and/or the apparatus is adapted to electrically isolate the work piece to be processed from the machine tool.

An inventive apparatus allows the monitoring of the tool by only measuring the electrical resistance between the spindle and the work piece which is different from the above discussed systems of the prior art. Furthermore, an inventive apparatus allows detecting the breakage of the tool during the processing process, preferably in real time. Thus, suitable counteractions can immediately be initiated as for example turning off the tool and/or the rotation of the tool, whereby subsequent damages of the tool breakage can be minimized for the work piece but in particular for the machine tool.

The disconnection of the electrical ground of the machine tool at one of the two measurement points of the electrical resistance measurement is the only prerequisite for the integration of an inventive apparatus in a machine tool. By the isolation of one measurement point from the electrical ground of the machine tool, it is possible to apply a defined voltage between the spindle and the work piece by which the ohmic resistance can be measured between the spindle and the work piece. The integration of the defined apparatus in a machine is very simple. The apparatus can be designed using conventional standard components. Furthermore, the operation of an inventive apparatus is also very simple and thus very robust.

In particular, an inventive apparatus does not interfere with the processing process of the machine tool. No measurement times are needed during which the machine is not available for the processing process, and thus the throughput of the machine is not adversely influenced. Thus, an inventive apparatus allows an economic monitoring of the operation of an electrically conductive tool of a machine tool and of an electrically conductive work piece to be processed.

Various portions of the machine are on different electrical potentials when disconnecting the electrical ground of the machine tool at a position and when applying an electrical voltage at the spindle and/or the work piece or the work bench of the machine tool. The voltages and currents which are used for a reliable measurement of the electrical resistance between the spindle and the work piece are so low so that they cannot impair the operation of the machine tool. However, it is still much more important that the different potentials of the machine are without any danger for the operating personnel and cannot damage the operation personnel.

An inventive apparatus uses voltages which are in the low voltage range, preferably below 30 V. The amount of current can be limited by the integration of a suitable current limiter, for example in form of a resistance. Further, in the case of an unintended short circuit, the amount of current can also be limited to a level which can neither damage the machine nor the operating personnel.

According to a further aspect the apparatus further comprises a voltage divider having at least two resistances, wherein the center tap of the voltage divider is conductively connected with the spindle and the detector, and wherein one end of the voltage divider is conductively connected with the work piece.

The size of the measurement signal can be adapted to the size of the resistance to be measured by a suitable choice of the resistances of the voltage divider. The application of a voltage divider automatically integrates a current limitation in an inventive apparatus. Furthermore, a current source can be used instead of a voltage source in the detector in an embodiment of the apparatus which uses a voltage divider.

According to a further aspect, the spindle comprises a spindle housing and a spindle tool holder, wherein the spindle housing is electrically isolated with respect to the machine tool and is connected to the detector or the center tap of the voltage divider.

In another aspect, the detector is operable to generate an alarm. In very simple versions of an inventive apparatus the detector outputs an acoustical and/or an optical alarm signal after the detection of a fault of the operation of the machine tool. This signal enables the operating personnel to control the operation state of the machine and to initiate respective counteractions. In machines which are designed for an automated or largely automated operation the detector supplies the detected fault to the monitoring system of the machine and the monitoring system automatically initiates the respective measures.

According to a further aspect the machine tool comprises several spindles electrically isolated from the machine tool.

Modern machine tools often comprise several spindles. For each spindle an own monitoring apparatus can be used. Furthermore, the design of the apparatus can be adapted to the design of the respective spindle. In an alternative embodiment several electrically isolated spindles can be connected to a single apparatus measuring the resistance. In order to secure a reliable monitoring of the simultaneous operation of several spindles, the detector is respectively adapted. In another aspect, the work piece is arranged on an electrically conductive work bench of the machine tool, and the detector is conductively connected with the work bench.

It is an advantage of this embodiment that the electrical contact to the detector has not to be removed from the work piece to be processed when the processing of the work piece has been finished and a work piece newly to be processed has not to be contacted before starting its processing. Thus, it is not possible to forget the electrical contacting of the work piece when manually operating an inventive apparatus.

In a preferred aspect, the work piece is arranged on an electrically isolated work bench of the machine tool, or the electrically conductive workbench is electrically isolated from the machine tool and the detector is conductively connected with the work piece or with the electrically conductive work bench which is electrically isolated from the machine tool.

In this design of an inventive apparatus the spindle or the spindle housing has not to be disconnected from the electrical ground of the machine tool. In a very simple design it is sufficient to disconnect an electrically non-conductive or an isolating support between the work bench and the work piece to electrically separate the latter one from the ground of the machine tool. In this way, the effort to integrate an inventive apparatus into an already existing plant is reduced to a minimum.

In a further preferred aspect, a work piece clamping device which clamps the work piece on the work bench in a way that it is electrically isolated from the machine ground has the advantage that the electrical ground of the machine tool has not to be changed. The replacements of the machine are limited to the exchange of the clamping device for the work piece. Furthermore, a professional electrically isolated clamping device secures that on the one hand the work piece is securely fixed, and on the other hand that the potential of the work piece is reliably separated from the electrical ground of the machine tool.

According to another aspect, the detector comprises a current detector and a voltage source, or the detector comprises a voltage source or a current source and a voltage detector.

An apparatus for measuring the resistance between the spindle and the work piece can be constructed from conventional standard components. These components with the required ranges are commercially available. Thus, the apparatus for an existing machine can be optimally designed. The required standard components are manifold tested, reliable and cost-effectively available.

In a further preferred aspect, the detector is operable to determine that the spindle, the tool and the work piece (a) form a first electrical resistance if the tool is not in contact with the work piece, or if there is no tool or work piece available, (b) form a second electrical resistance if the tool is in contact with the work piece, or (c) form a third electrical resistance if the tool is in contact with the work piece and the tool and/or the work piece are defective.

The measurement of the electrical resistance between the spindle housing and the work piece provides numerical values in three different ranges. The first electrical resistance $R_1$ is essentially infinite, since the contact resistance between the tool and the work piece which are not in contact with each other (i.e. they are separated by an air gap from each other) causes this numerical value. In this context as well as at the further explanations of this description an infinite resistance means a numerical value of the ohmic resistance which is above the measurement limit of the applied detector.

The second electrical or ohmic resistance $R_2$ is in the range of several $\Omega$ to several $k\Omega$, and is predominantly determined by the contact resistances between the spindle tool holder and the work piece and between the work piece and the work bench. The third resistance $R_3$ has numerical values in an interval reaching from the $k\Omega$ range to the $G\Omega$ range. Generally, the numerical values of the ohmic resistance are related: $R_1 \geq R_3 > R_2$.

In still another preferred aspect, the detector is further operable to determine that an incorrect tool or an incorrect work piece exists if a transition from the first electrical resistance to the second electrical resistance occurs at a distance between the spindle and the work piece which is larger than a predetermined distance. According to a further aspect, the detector is also operable to determine that a correct operation of the machine tool exists if the transition from the first electrical resistance to the second electrical resistance occurs within a predetermined distance interval between the spindle and the work piece. In still another aspect, the detector is operable to determine that the tool is missing if no transition from the first electrical resistance to the second electrical resistance occurs within a predetermined distance interval between the spindle and the work piece. According to a further beneficial aspect, the detector is further operable to determine that an incorrect tool or an incorrect work piece exist if a transition from the first electrical resistance to the second electrical resistance occurs at a distance between the spindle and the work piece which is smaller than a predetermined distance. In still another aspect, the detector is further operable to determine that a defective tool or a defective work piece exist if a transition from the second electrical resistance to the third electrical resistance occurs.

Thus, an inventive apparatus cannot only be used to determine the missing of a tool or a breakage of a tool of a machine tool. Rather, the above defined apparatus can also be used to detect whether the inserted work piece is correctly positioned or whether the correct tool is available in the machine.

In still a further aspect, the detector is adapted to monitor that the behavior of the electrical resistance essentially follows a predetermined behavior when processing the work piece. According to another preferred aspect, the behavior of the electrical resistance when processing the work piece is below a first predetermined envelope and above a second predetermined envelope. In another beneficial aspect, the behavior of the electrical resistance when determining the work piece is within predetermined area values.

Different from the above explained simple embodiment in which the detector generates an alarm, the detector can comprise the function to forward its resistance measurement data to a monitoring system of the machine tool after a respective preparation. The monitoring system of the machine or its display or monitor visualizes the behavior of the resistance measurement in a manner in which further operation characteristics of the machine are also presented on the display. Thus, the measurement data of an apparatus for resistance measurement between the spindle and the work piece can be illustrated in a form which is familiar for the operating personnel with.

According to a further aspect, the detector is coupled to a monitoring system of the machine tool and the monitoring system is designed to interrupt the operation of the machine tool.

By feeding back an inventive apparatus with the monitoring system of the machine tool, the machine tool can virtually react in real time to measurement results of the resistance measurement of the detector. If necessary, the monitoring system turns off the feed and/or the rotation of the tool with a minimum time delay. The subsequent damages occurring at the work piece and/or at the machine when detecting a tool breakage can thus be reduced to a minimum.

The data transfer between the detector and the monitoring system is not to necessarily restricted to one direction. Rather, the detector can be designed that it is controllable by the monitoring system of the machine.

Finally, in a particularly preferred aspect, when processing an electrically conductive work piece, a method for monitoring a machine tool with an electrically conductive spindle comprises the step of determining a modification of the electrical resistance between the spindle and the work piece. In this process, the spindle holds an electrically conductive tool and the spindle and/or the work piece is electrically isolated from the machine tool.

Further embodiments of the invention are described in further dependent claims.

4. SHORT DESCRIPTION OF THE FIGURES

The following detailed description describes presently preferred embodiments of the present invention with reference to the accompanying figures wherein.

5. DETAILED DESCRIPTION OF PREFERRED EMBODIMENTS

In the following presently preferred realization examples of the inventive apparatus and of the inventive method for monitoring a machine tool are explained in more detail. Thereby, these examples are described in the context of the machine tool with a spindle and a tool. However, an application in other machine tools is also possible.

Figure 1:
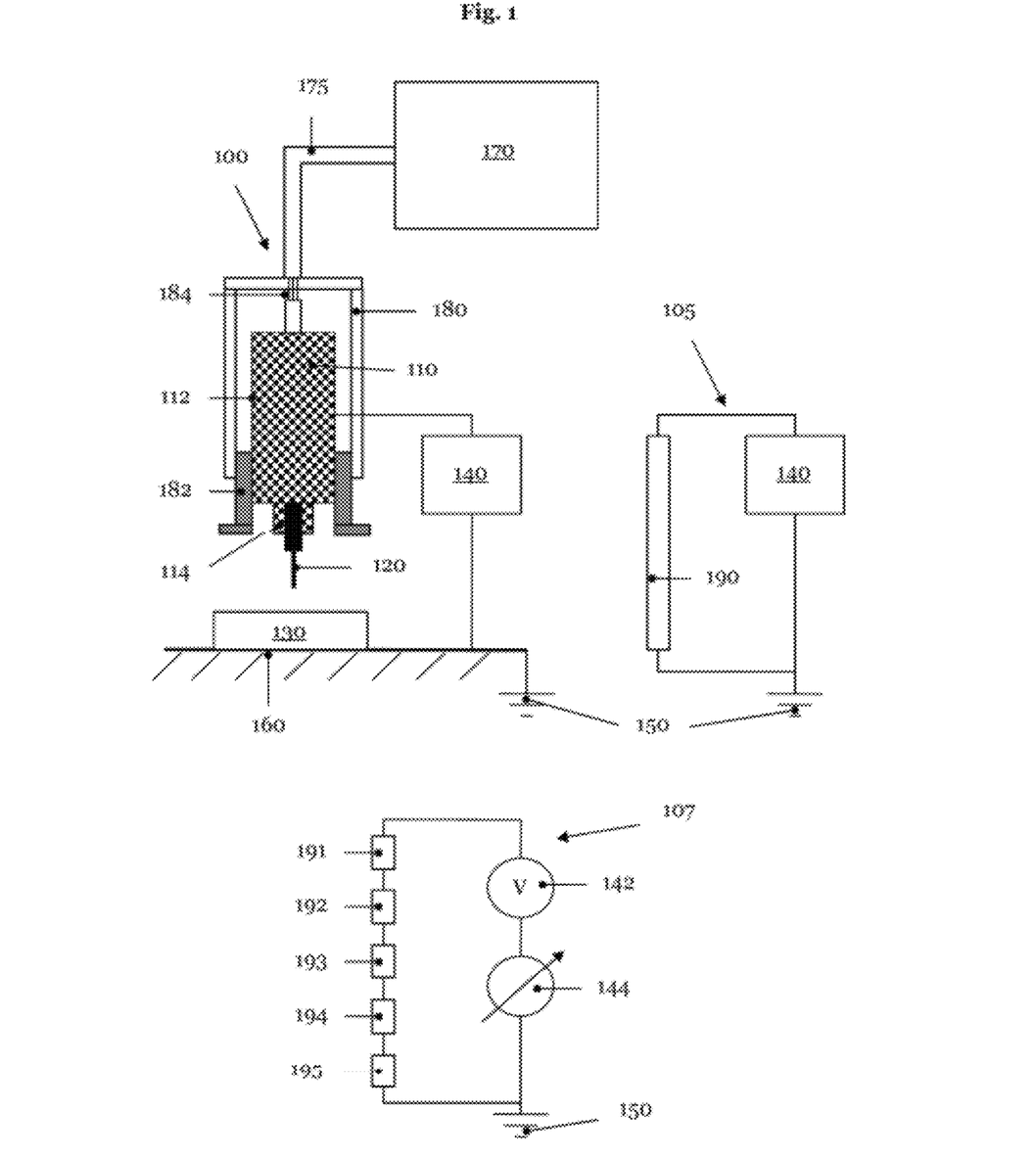
FIG. 1 illustrates a schematic representation of some components of a machine tool, the work piece and an integrated inventive apparatus (left upper partial image), shows the electrical equivalent circuit diagram of some components of the machine tool (right upper partial image) as well as illustrates a simple realization example of an apparatus for resistance measurement (lower partial image)

FIG. 1 in the left upper partial image) shows the schematically representation of some important components of a machine tool 100. The machine tool 100 has a spindle 110 with a spindle housing 112 and a tool holder 114. The spindle housing 112 and the tool holder for the tool 114 are conductively connected with each other. A bushing insulator 182 separates the protection housing 180 of the housing 112 of the spindle no, wherein the bushing insulator 182 has electrically isolating material at least at the outsides.

The convertor 170 supplies electrical power to the spindle 110. The electrical ground of the supply line 175 is connected with the protective housing 180 of the spindle 110 and the phases 184 of the electrical supply line 175 are supplied to the spindle 110. Thus, the spindle housing 112 is electrically decoupled from the electrical ground of the machine tool 100. However, the protective housing 180 of the spindle 110 is connected to the electrical ground 150 of the machine tool 100 (machine ground 150).

An electrically conductive tool 120 is inserted in the tool holder 114. In the example represented in FIG. 1, the tool holder 114 carries a drill. However, the tool holder 114 of the spindle 110 is not restricted to the insertion of a drill. Rather, the spindle 100 can hold all kinds of rotating tools 120 as for example milling cutters, roaching tools or thread cutters.

The tool 120 is directed to the work piece 130 to be processed which is arranged on the work bench 130 of the machine tool 100. The work piece 130 has to be electrically conductive. Thus, the application of an embodiment of the apparatus allows the measuring of the resistance between the spindle and the work piece; in particular for all kinds of metallic work pieces, alloys or cast parts. The work piece 130 to be processed has not to fulfill further requirements. In the example of FIG. 1 the electrical ground 150 of the machine tool 100 (machine ground 150) is combined at the work bench 160.

The detector 140 is integrated or connected between the electrically isolated spindle housing 112 of the spindle 110 and the work bench 160 of the machine tool 100. The electrical equivalent circuit diagram 105 of the parts relevant for the resistance measurement of the machine tool 100 and of the detector 140 is represented in the right upper partial image of FIG. 1.

The detector 140 measures the electrical resistance 190. The realization example illustrated in the lower partial image of FIG. 1 shows a very simple design of the detector 140 and schematically shows the essential components of the resistance 190 of the equivalent circuit 105. In the simple realization example 107 presented in FIG. 1, the detector 140 comprises a voltage source 142 and a current detector 144 in form of an ampere meter or a current meter connected in series with the voltage source 142. According to Ohm's law the numerical value of the resistance 190 is determined from the quotient of the potential difference generated by the voltage source 142 and the current measured with the ampere meter 144.

In the shown embodiment the voltage source 142 is simply a DC (or a direct current) voltage source which generates a fixed or an adjustable voltage at its output. The amplitude of the potential difference generated by the voltage source 142 depends on the one hand from the magnitude of the resistance 190 to be measured and on the other hand from the distortions generated by the machine tool 100 or its environment. The numerical value of the electrical voltage applied to the spindle housing is in the range of up to 50 Volts for spindles with ball bearings or roller bearings. Preferably the standard machine voltage of 24 V is used for these spindles.

The voltage source 142 of the detector 140 can have a resistance connected in series (not depicted in FIG. 1) in order to limit the current to a predetermined level also in case of a short circuit. In other embodiments, the voltage source 142 can generate an alternating voltage of a suitable frequency. Alternatively, the voltage source 142 can output a digital pulse sequence. The sensitivity of the current measurement or the voltage measurement can be increased also in an environment contaminated by HF noise by using a suitable carrier frequency and by a respective adaptation of the ampere meter 144.

In a simple embodiment, the detector 140 comprises beside a voltage source 142 and a current detector 144 at least one element in order to generate an alarm signal (not shown in FIG. 1). The element for generating the alarm signal can generate an acoustic and/or an optical signal.

The realization example 107 indicates the essential components of the resistance 190 of the electrical equivalent circuit 105. The resistance 191 represents the electrical resistance of the spindle 110, i.e. the ohmic resistance from the spindle housing 112 to the tool holder 114 of the spindle 110. The resistance 191 comprises apart from the resistance of the spindle housing 112 and the tool holder 114 also the resistance of the bearings of the spindle and the contact resistances between the individual components of the spindle. In particular, the electrical resistance within the bearings which comprises rotating components is strongly dependent on the individual set-up of the bearings and of its operating state. For these reasons the resistance 191 of the spindle significantly fluctuates. Furthermore, the resistance 191 can comprise a temporary and/or a permanent parallel resistance which is caused by coolants, oil and/or dirt on the spindle. However, the resistance 191 for spindles having ball bearings or roller bearings of metal components is always in the low ohmic range, i.e. <1 k$\Omega$. The contact resistance between the spindle housing 112 and the axle or the tool holder 140 can be significantly higher for spindles no having magnetic bearings or ceramic bearings.

The resistance 193 takes the ohmic losses within the tool 120 into account. Since the tool 120 is regularly fabricated from hard or hardened metal or metal alloys, the resistance of the tool is typically small; its numerical value depends on the material as well as on the geometry of the tool 120 and is typically in the range of some m$\Omega$ to some $\Omega$. Thereby, the coating of the tool 120 has a significant influence on its ohmic resistance 193.

The resistance 195 takes into account the electrical resistance of the work piece 130. The material of the work piece 130 as well as of the geometry for conventional work pieces 130 determines the resistance 195, i.e. for work pieces which are processed in large quantities the numerical value of the resistance 195 is below 1 k$\Omega$.

The resistance 192 represents the contact resistance or the transition resistance between the tool holder 114 of the spindle 110 and the shaft of the tool 120. The numerical magnitude of the resistance 192 depends on the size of the contact area between the tool holder 114 and the shaft of the tool 120. Furthermore, the resistance 192 depends essentially on the surface appearance of the two components 120 and 130 as well as if applicable on an available coating of the tool 120. The contamination of the tool holder 114 and/or of the tool 130 can impair the contact resistance 192. Typically, the numerical value of the contact resistance 192 is larger than the numerical values of the resistances 191, 193 and 195 of the individual components spindle 110, tool 120 and work piece 130 and can reach the high ohmic range, i.e. >1 k$\Omega$ at a large degree of contamination.

Finally, the resistance 194 takes into account the contact resistance or transition resistance between the tool 120 and the work piece 130. In the arrangement of the machine tool 100 in FIG. 1, the tool 120 is not in contact with the work piece 130 so that the numerical value of the resistance 194 is essentially infinite. Therefore, the resistance 119 which combines a series resistance of the resistances 191, 192, 193, 194 and 195 is essentially the numerical value of the contact resistance 194. This value of the resistance 190 is in the following called $R_1$ as already introduced in the third part of the description. The current generated by the voltage source 142 and measured by the ampere meter 144 is essentially zero, i.e. except for possibly occurring leakage currents.

Figure 2:
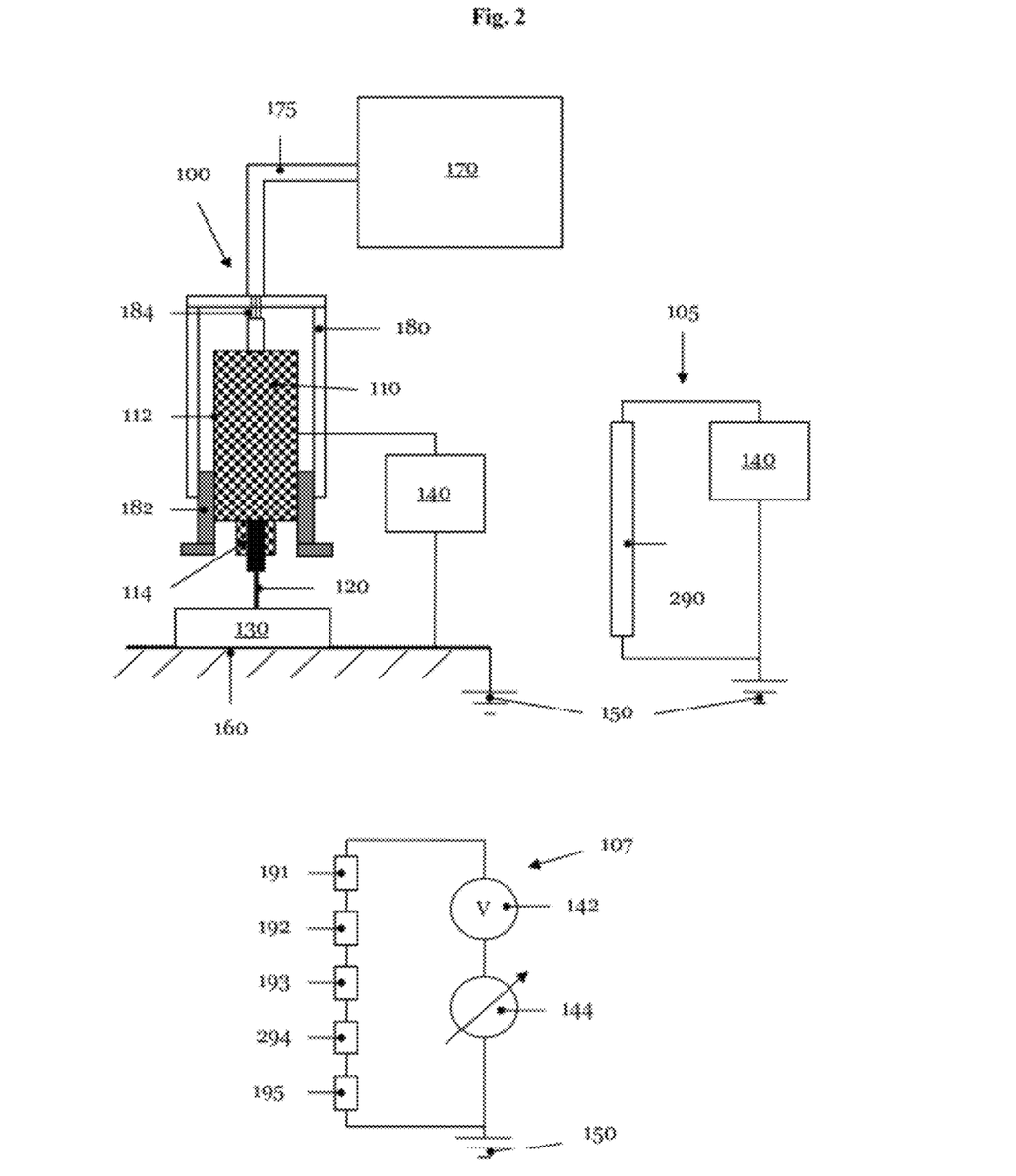
FIG. 2 illustrates FIG. 1 wherein the tool of the machine tool is in contact with the work piece.

FIG. 2 shows the machine tool 100 of FIG. 1 in which the tool 120 is in mechanical contact with the work piece 130. Thus, the contact resistance 294 changes its numerical value from essentially infinite (resistance 194 of FIG. 1) to a finite resistance value. The contact area between the tool 120 and the work piece 130 as well as the surface geometry of the tool 120 influences the contact resistance 294. Furthermore, an applied coolant may have an important influence on the magnitude of the resistance 294. Therefore, the numerical value of the resistance can fluctuate across a broad interval of numerical values. This interval can extend from a few Ω to the range of kΩ.

In the following this value of resistance 290 is called $R_2$. It is identical with the electrical resistance $R_2$ already introduced in the third section. It can be determined by means of the ampere or current meter 144 of the detector 140 when the voltage source 142 is switched on.

Figure 3:
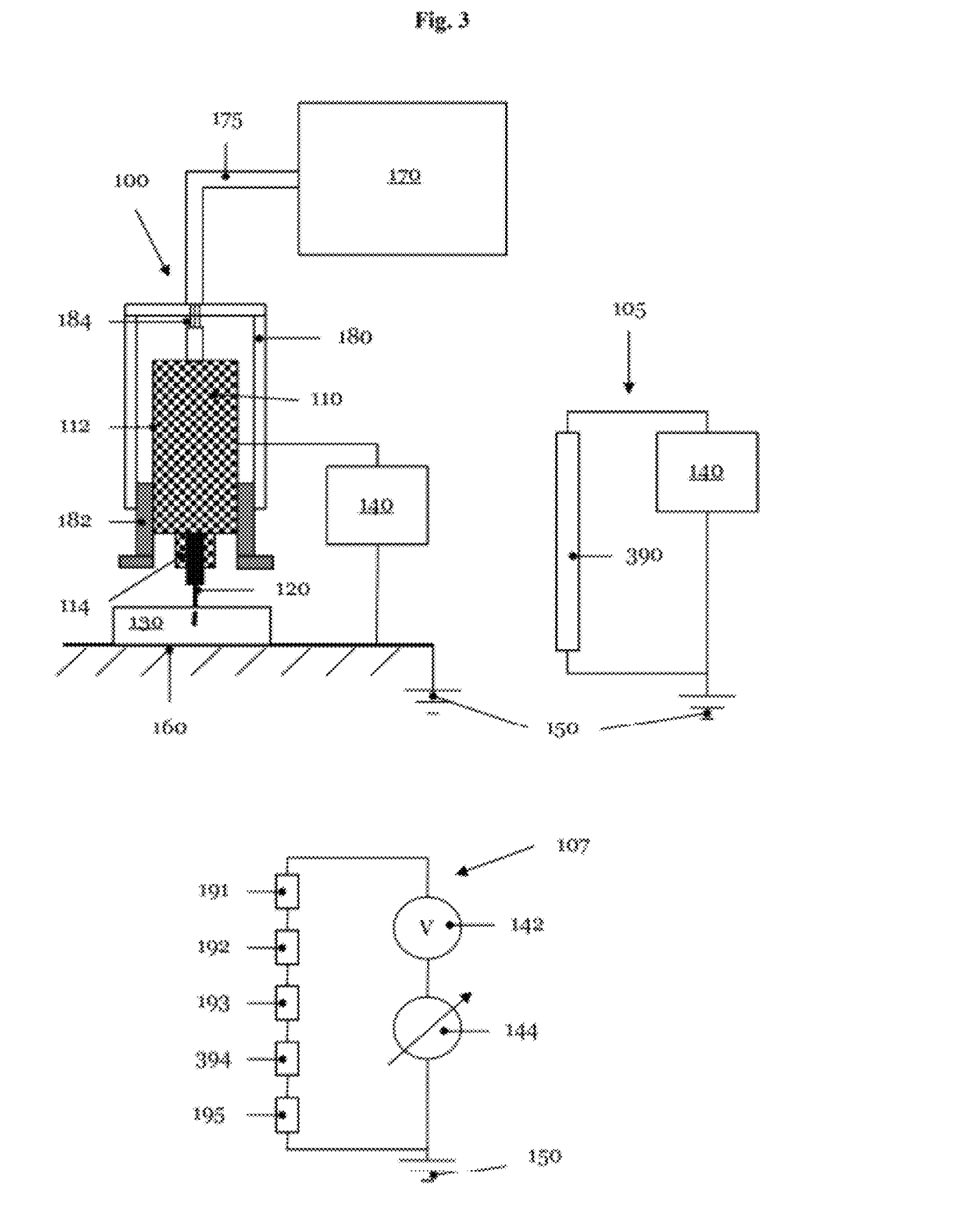
FIG. 3 represents FIG. 1 after the tool is broken during a drilling process.

FIG. 3 illustrates the situation when the tool 120 breaks during a drilling process of the machine tool 100, i.e. the drill breaks. The breakage of the tool 120 changes the contact resistance 394 between the tool 120 and the work piece 130. As a rule, a breakage of the tool 120 impairs the contact to the work bench 130, and thus leads to an increase of the contact resistance 394 between the (defective) tool 120 and the work piece 130. This leads to an increase of the contact resistance 394 in comparison to the situation represented in FIG. 2 (resistance 294). A similar situation may occur when the work piece 130 breaks but not the tool 120. Thus, the resistance 394 can fluctuate across a large range of values depending on the individually occurring defect. Apart from extreme cases the numerical value of the resistance 394 is typically in the kΩ up to the GΩ to range. For the rest of this description, the resistance 390 is called $R_3$. It corresponds to the resistance $R_3$ introduced in the third section of the description.

A DC current measurement or a DC voltage measurement for determining the resistance 190, 290, 390 can be hampered by high frequency distortions generated by the machine tool 100 or the environment as already discussed above. The spindle 110 is part of the signal path of the measurement signal in the apparatuses for analyzing the resistance between the spindle 110 and the work piece 130. The spindle 110 has stationary parts (for example the spindle housing 112) and rotating parts (for example the tool holder 114). Thus, the spurious or distorted signals generated by the spindle 110 are superimposed in an unfiltered way the measurement signal. Therefore, it has been demonstrated as appropriate to insert a low pass filter in the detector 140 in order to suppress to a large extent the high frequency spurious or distorted noise superimposed to the measurement signal (not shown in FIGS. 1 to 3).

Figure 4:
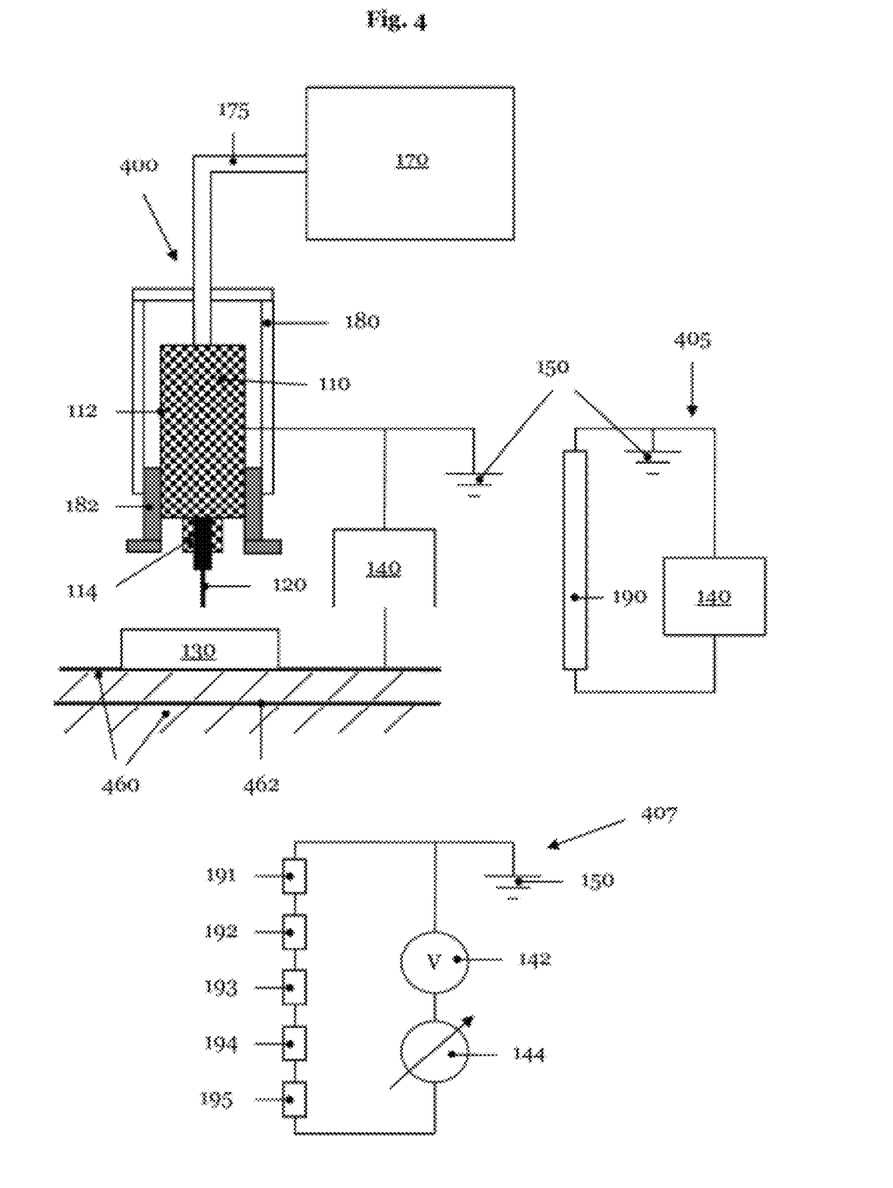
FIG. 4 repeats FIG. 1 at which the electrical ground is not disconnected at the spindle of the machine tool but at the work bench of the machine tool.

The measurement of the resistance 190, 290 and 390 with the detector 140 requires the disconnection of the electrical ground 150 of the machine tool 100 at one of the two measurement positions. In FIGS. 1 to 3 the housing 112 of the spindle 110 of the machine tool 100 is separated from the electrical ground 150. However, this separation can also occur at the second measurement position. FIG. 4 illustrates this embodiment in the left upper partial image. An electrically isolating layer 462 is inserted in the work bench 460 of the machine tool 400. Thereby, the upper part of the work bench 460 is electrically separated from the machine ground 150. In this embodiment it is not necessary to disconnect the spindle housing 112 from the machine ground 150. The right upper partial image of FIG. 4 represents the electrical equivalent circuit 405 of this embodiment of the apparatus for resistance measurement. The realization example 407 of the lower partial image of FIG. 4 shows the realization example 107 of FIG. 1 in which the ground connection 150 is shifted to the other terminal.

In a particularly simple embodiment, the machine tool 100, 400 itself is not changed. Rather, the work piece 130 is simply electrically separated from the machine ground 150 by an isolating support and the work piece 130 and is directly connected with a terminal of the detector 140 (not shown in this Figure). This embodiment reduces the integration effort of the apparatus into the machine to a minimum, and is thus suitable in particular for upgrading plants which are already in use.

A further simple embodiment does not change the machine ground 150 of the machine tool 100, 400 with respect to its initial state. The disconnection of the electrical ground for measuring the resistance 190, 290, 390 occurs at a tool clamping device which clamps the work piece 130 in an electrically isolating manner. This embodiment can at least be realized in two variants. On the one hand, the clamping jaws and the clamping claws can be isolated against the other parts of the clamping device. This variant of an isolating clamping device for measuring the resistance 190, 290, 390 between the spindle 110 and the work piece 130 can be integrated with minimum effort in a machine tool. On the other hand, the tool clamping device can be electrically isolated from the work bench 160 of the machine tool 100, 400 by an electrically isolating plate and electrically isolating threaded sleeves. This variant may require replacement efforts for the machine tool 100, 400.

It is also conceivable to separate both terminals from the machine ground 150 for the integration of a detector 140, i.e. to combine the embodiments of the machine tools 100 and 400.

Figure 5:
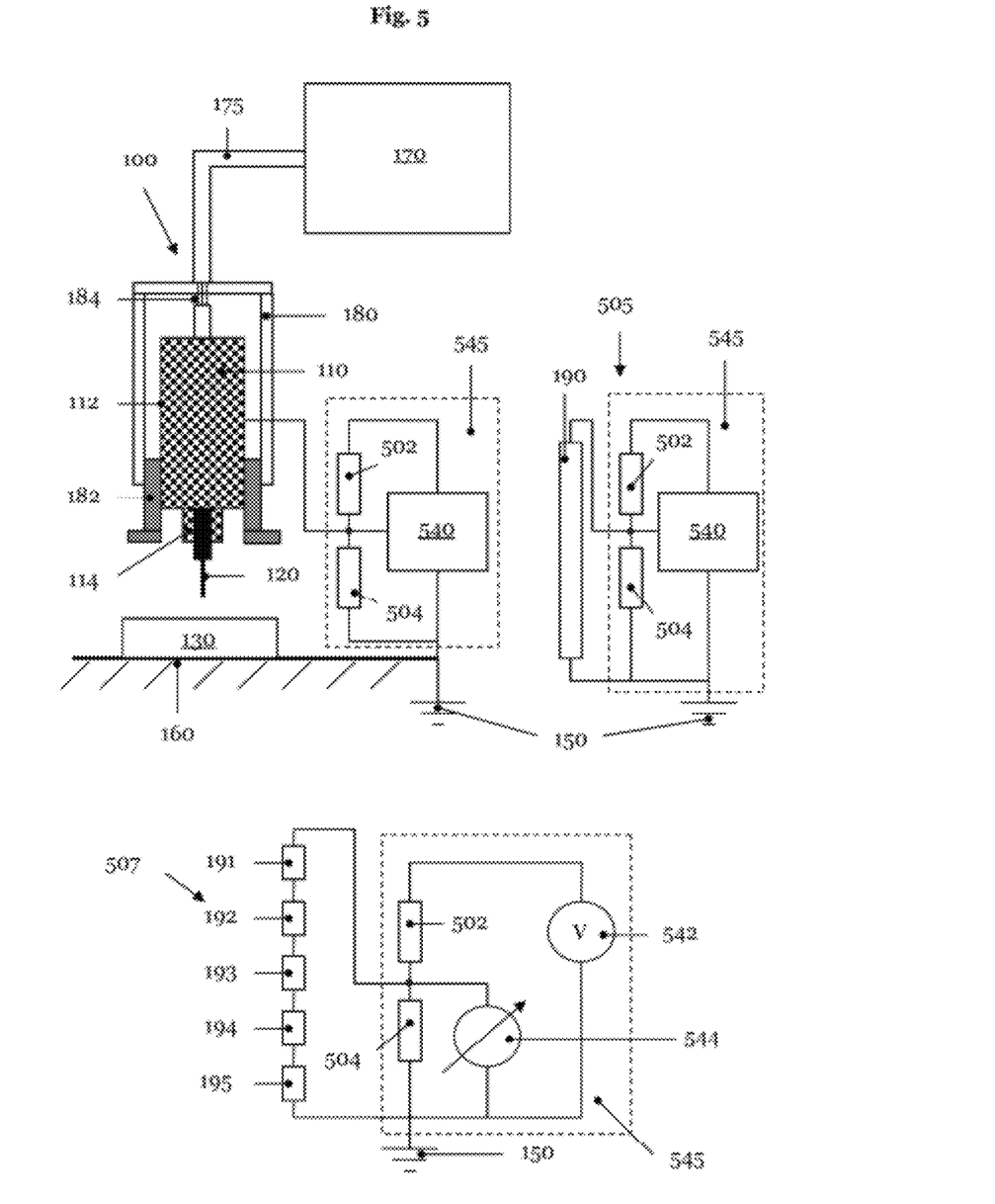
FIG. 5 represents FIG. 1 at which the detector for measuring the resistance additionally comprises a voltage divider which is inserted between the measurement points at the machine tool and the measuring detector.

FIG. 5 shows in the left upper partial image the machine tool 100 of FIG. 1 at which the detector 140 is replaced by a modified resistance detector 540 and a voltage divider. Thus, the detector 545 comprises the voltage divider of the resistances 502 and 504 as well as the detector 540 for the resistance measurement. The right upper partial image depicts the electrical equivalent circuit 505 and the lower partial image represents a realization example 505 of the detector 545.

The voltage divider comprises two resistances 502 and 504. In the embodiment indicated in FIG. 5, a voltage source 542 generates a potential difference which is applied to the voltage divider. The explanations given above for the voltage source 142 of FIGS. 1 to 4 analogously apply for the voltage source 542. The resistance 502 of the voltage divider is for example in the one digit kΩ range and simultaneously serves as a current limiter in case of a short circuit of the resistance 190. The resistance value of the second resistance 504 of the voltage divider is adapted to the resistance 190 between the spindle 110 and the work bench 130. In an exemplary embodiment of the voltage divider the numerical value of the resistance 504 is in the range of 100Ω. The center tap of the voltage divider is connected to the spindle housing 112 of the spindle 110, and is thus connected with a terminal of the resistance 190. The voltage detector 545 determines the value and the temporary behavior of the resistance 190 via the center tap of the voltage divider.

Instead of a voltage source 542 a current source can be used in the detector 545. FIG. 5 does again not show the alarm generator in the detector 545.

In the example represented in FIG. 5, the detector 545 is integrated in the machine tool 100 of FIG. 1. In a further embodiment, the detector 545 can be integrated in the machine tool 400 of FIG. 4.

Figure 6:
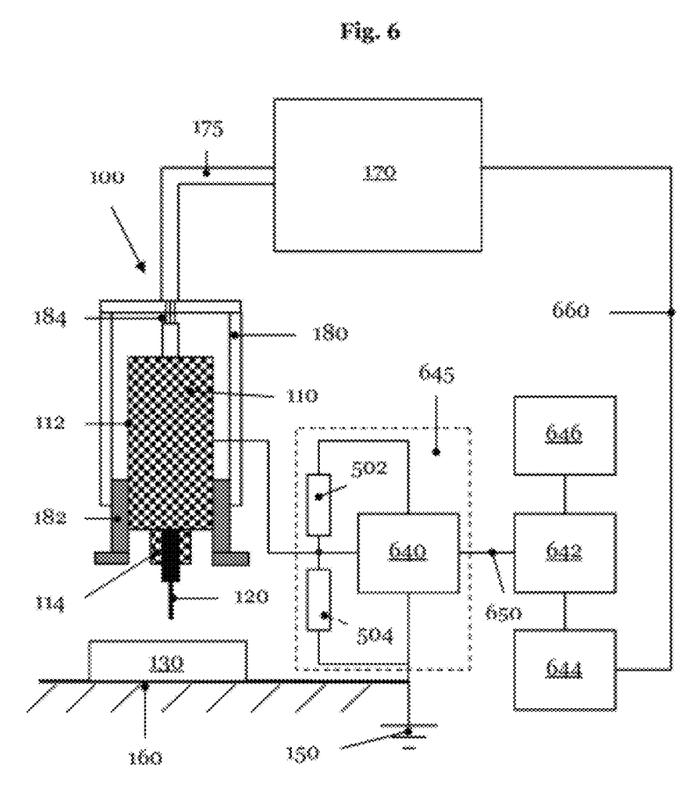
FIG. 6 represents FIG. 5 at which the detector is connected to the monitoring system of the machine tool.

FIG. 6 reproduces the machine tool 100 with a detector 645 which again comprises a voltage divider. The detector 645 is connected to the monitoring system 642 of the machine tool 100, 400 via the connection 650. The monitoring system 642 is in turn connected with the NC (numerical control) control 644 of the machine tool 100, 400. Furthermore, the NC control 644 is connected with the convertor 170 of the machine tool 100, 400 via the connection 660. For this reason, the monitoring system 642 can turn off the convertor 170 of the machine tool 100, 400 via the NC control 644, and can thus stop the feed of the spindle 110 and if required the rotation of the tool 120.

The detector 645 transfers the temporary behaviors of the numerical values of the resistances 190, 290 and 390 measured during the operation via the transmission path 650 to the monitoring system 642. The transmission can be transformed wirelessly or wired. The measurement data can be transmitted from the detector 645 to the monitoring system 642 in analogue or digital form.

The data transmission has not to be restricted to one direction. Rather, the connection 650 between the detector 645 and the monitoring system 642 can be used for controlling the detector 645 by the monitoring system 642.

Moreover, the monitoring system 642 is connected with a display. Apart from further characteristics, the display of the machine tool also enables the graphical representation of measured resistance behaviors of the resistances 190, 290 and 390.

The apparatus represented in FIG. 6 has been successfully used to control the operation of a machine tool 100, 400 which has a drill inserted in its spindle tool holder 140 having a diameter of 0.35 mm. The operation of the machine tool 100, 400 means here as well as in the following starting and stopping of the rotational motion of the tool 120 and a controlled changing of the distance between the spindle 110 and the work piece 130, i.e. the turn-on or turn-off of a defined feed of the spindle 110 and/or of the work bench 130.

Figure 7:
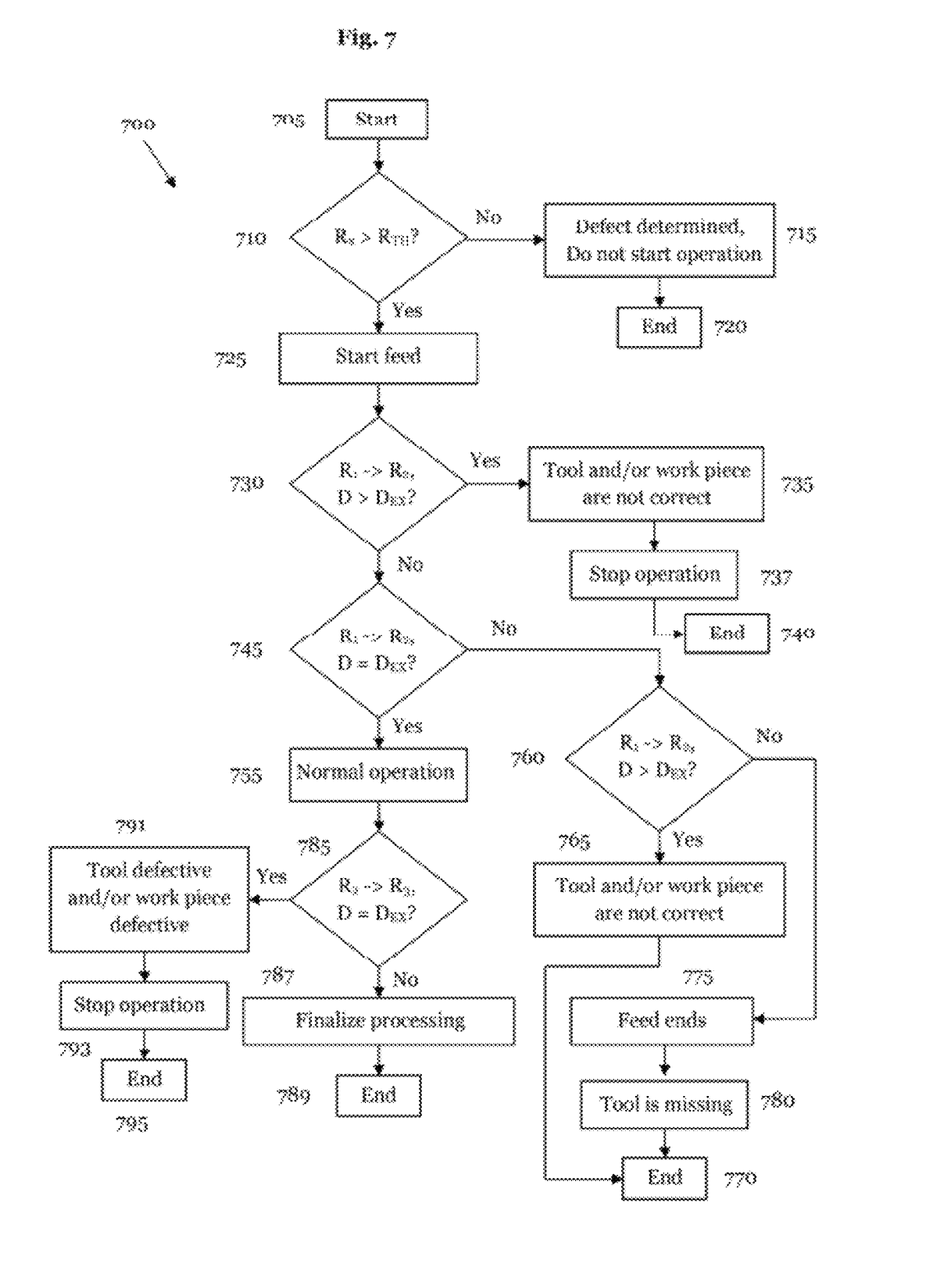
FIG. 7 schematically illustrates a flow diagram of the method of a realization example.

FIG. 7 schematically illustrates the flow diagram of an exemplary embodiment of the inventive method 700. This realization example is based on an arrangement in which the detector 645 transmits its measurement data to the monitoring system 642 and wherein the monitoring system 642 controls the machine tool 100, 400.

The method 700 begins at step 705. As it is illustrated in the FIGS. 1, 4, 5, and 6, in the initial situation the tool 120 is not in contact with the work piece 130. Thus, as explained above, the resistance 190 is essentially infinite. Furthermore, the rotational motion of the tool 120 is not turned-on at the start position.

At decision block 710, the resistance 190, 290, 390 is sampled. The resistance 190, 290 and 390 is in the following noted as $R_x$. It is assumed that there is a fault of the machine tool 100, 400 as for example a short circuit, if it is determined at the sampling that a numerical value of the resistance $R_x$ does not exceed a predetermined threshold $R_{TH}$. This fault is indicated to the user via the display or the monitor 646 and the operation of the machine tool 100, 400 is not started, i.e. the turn-on of the rotation of the tool 120 and the turn-on of the feed by which the distance between the tool 120 and the work piece 130 is diminished in a controlled manner. Rather, the method ends at step 720.

The control 644 starts the operation of the machine 100, 400 at step 725 by turning on the rotation of the tool 120 and of the feed, if it is determined at decision block 710 that the measured resistance $R_x$ is larger than the threshold $R_{TH}$.

Figure 8:
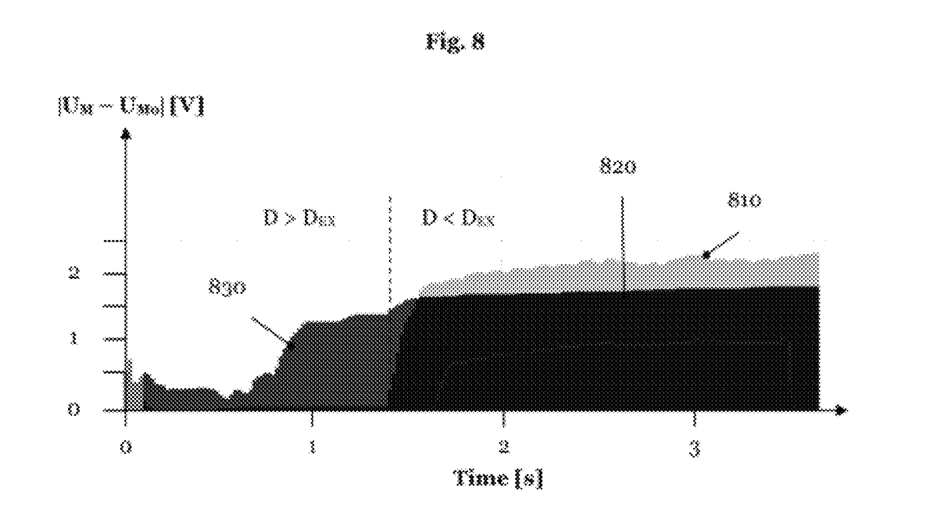
FIG. 8 illustrates the behavior of a representation of the resistance measurement signal when the work piece is too high with respect to the position to be processed and/or the spindle has the wrong tool (process is not okay)

The monitoring system 642 stores the data at which distance between the spindle 110 and the work piece 130 a mechanical contact between both components should occur as a function of the tool 120 used for the processing of the work piece 130. In FIG. 8, this value is indicated as $D_{EX}$. It is expected that the resistance $R_X$ changes its numerical value from $R_1$ into $R_2$ at this position, since the contact resistance 194 (FIG. 1) transmits from an essentially infinite resistance to the resistance 294 having a finite numerical value. Alternatively and/or additionally to the storage of the $D_{EX}$ data in a memory of the machine tool 100, 400, the distance D between the spindle 110 and the work piece 130 can be continuously or periodically be measured.

The display 646 of the monitoring system 642 shows to the user at block 735 that either the work piece 130 or the tool 120 is not correct, if it is determined at decision block 730 of FIG. 7 that the transition of the resistance $R_X$ from $R_1$ to $R_2$ occurs at a distance D between the spindle 110 and the work piece 130 which is larger than the expected distance $D_{EX}$. An example of an incorrect tool exists for example if a milling cutter is erroneously clamped in the tool holder 140 of the spindle 110 instead of a drill, or if the length of the clamped drill is not correct. A defective work piece is for example a work piece which is not at the correct position relative to the tool 120, or if the work bench 160 has a work piece 130 having a too large thickness.

When at step 737 the condition of the decision block 730 is fulfilled, the operation of the machine 100, 400 is stopped and the method ends at step 740 in order to minimize the damage of the work piece 130 and the follow-up costs of a wrong processing.

FIG. 8 schematically shows a representation of the behavior of a voltage measurement at the center tap of the voltage divider of FIG. 5 at a measurement of the resistance $R_X$. For the applied voltage U the voltage $U_M$ measured with the voltage detector 544 is given by:

$$U_M = \frac{\frac{R_2 \cdot R_x}{R_2 + R_x}}{R_1 + \frac{R_2 \cdot R_x}{R_2 + R_x}} \cdot U \qquad (1)$$

wherein $R_1$ corresponds to the resistance 502 and $R_2$ corresponds to the resistance 504 of FIG. 5. For $R_x \to \infty$, i.e. $R_x = R_1$ equation (1) reduces to:

$$U_{M0} = \frac{R_2}{R_1 + R_2} \cdot U \qquad (2)$$

In FIG. 8 (as well as in the following FIGS. 9 and 10) the absolute value of the voltage $U_M$ is depicted relative to the situation in which the resistance 191 between the spindle 110 and the work piece 130 is infinite ($R_x = R_1$), i.e. $|U_M - U_{M0}|$ as a function of time in which the feed is turned on. In this representation an increase of the depicted voltage difference means a decrease of the voltage at the center tap of the voltage divider caused by a diminishing of the resistance 190 or of the resistance $R_X$. A transition from a zero voltage to a signal value within the area threshold value 810 should occur at the distance $D_{EX}$ at this kind of representation.

The light grey area 810 shows the expected area threshold value 810 of the voltage $|U_M - U_{M0}|$ for a correct tool 120 and a work piece 130. The black curve shows the measured voltage behavior for the range in which a mechanical contact is expected between the tool 120 and the work piece 130, i.e. for $D < D_{EX}$. The transition from $R_1$ to $R_2$ is expected at the beginning of this interval. The black area 820 represents a normal operation of the machine tool 100, 400; the depiction of the voltage $|U_M-U_{M0}|$ by the area 820 is below the area threshold value 810 during the entire processing process (i.e. $D<D_{EX}$). FIG. 8 shows that the measured voltage $U_M$ and thus the resistance $R_2$ is essentially constant during the processing process.

The middle gray range 830 illustrates that already at a distance interval $D>D_{EX}$ the transition occurs from $R_1$ to $R_2$. The left portion of the medium gray range 830 shows in detail the contacting between the tool 120 and the work piece 130. The contacting has been deliberately caused by applying of chips onto the surface of the work piece 130. In this distance range the numerical value of the resistance $R_X$ between the spindle 110 and the work piece 130 is still in the high ohmic range and also shows a significant fluctuation.

The right portion of the range 830 illustrates the change of the resistance $R_X$ caused by the start of the cutting of the material of the work piece 130. After a steep decrease of the resistance $R_X$ this resistance reaches the level of $R_2$ already in the range $D_{EX}$. This means that FIG. 8 shows a work piece 130 which is too high.

FIG. 8 illustrates a portion of the example of the inventive method explained in FIG. 7. For this reason, the operation of the machine 100, 400 is not interrupted after the detection of the transmission from $R_1$ to $R_2$ in the distance interval $D>D_{EX}$.

Again referring to FIG. 7, it is determined at the decision block 745 whether the transition from $R_1$ to $R_2$ occurs at the expected distance between the spindle 110 and the work piece 130. If this is correct the machine tool 100, 400 operates in a normal operation mode as is indicated in block 755 of FIG. 7.

Figure 9:
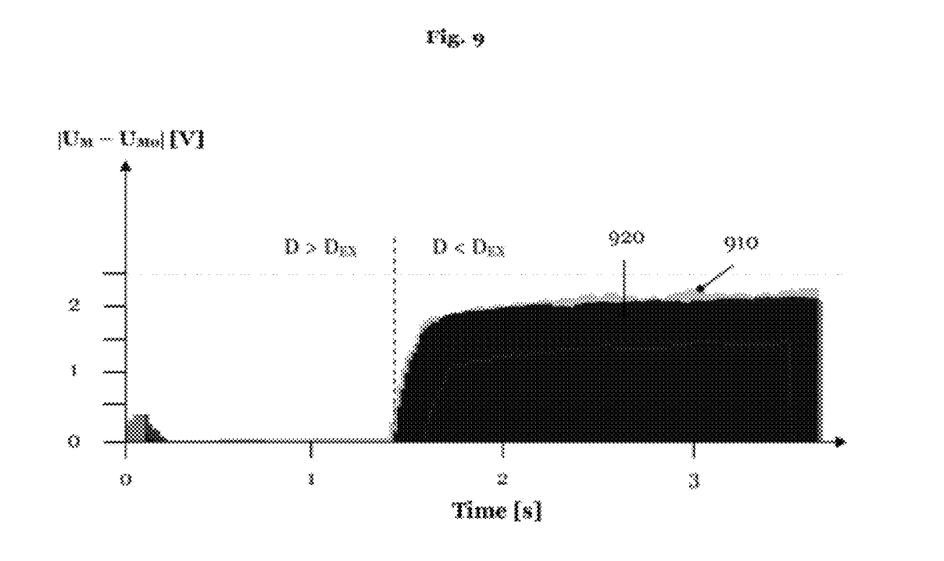
FIG. 9 shows an exemplary behavior of a resistance measurement signal for a normal behavior of the processing process (process is okay)

FIG. 9 illustrates a representation of the behavior of the measurement of the resistance $R_x$ during a normal processing process. As in FIG. 8, the ordinate depicts the absolute value of the voltage difference of $U_M$ and $U_{MO}$ as a function of the lapsed time since switching on the feed. In the distance interval $D>D_{EX}$, $R_X$ has the value $R_1$ ($U_M=U_{MO}$). The transition from $R_1$ to $R_2$ occurs at $D_{EX}$ as expected. The measured variable $|U_M-U_{M0}|$ is always below the predetermined area threshold value 910 in the region $D<D_{EX}$.

Again referring to FIG. 7, it is determined at decision block 760 whether the change can be determined in the distance interval $D<D_{EX}$ in the case that the transition from $R_1$ to $R_2$ is not detected at $D_{EX}$. If this is not the case, the feed ends at step 775 after the expiry of a predetermined feed interval and the display 646 shows at step 780 that the tool 120 is missing and the method ends at step 770.

Figure 10:
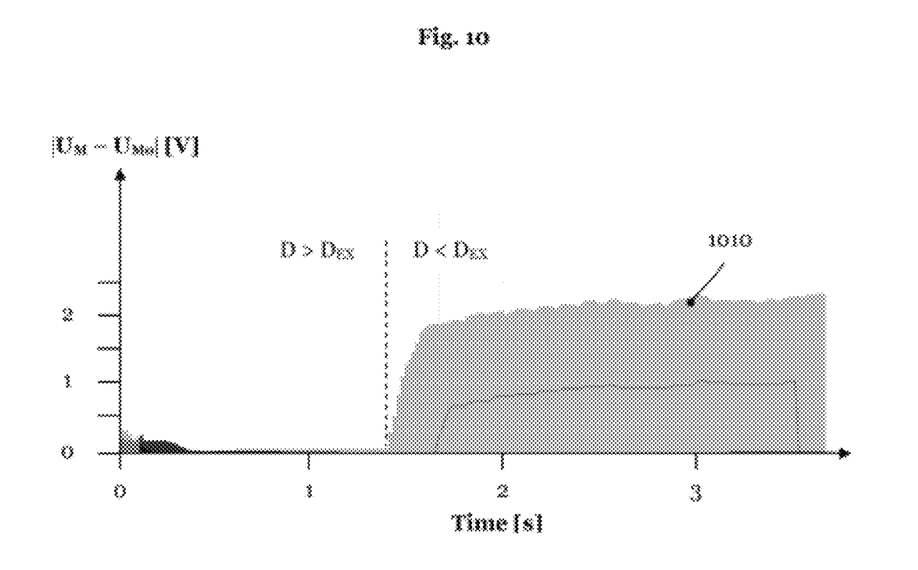
FIG. 10 to depicts the behavior of a representation of the resistance measurement signal when the tool holder of the spindle does not have a tool (process is not okay).

FIG. 10 illustrates this situation. The gray area 1010 again represents the to area threshold value for the resistance $R_x$, wherein the measured value is again given by $|U_M-U_{M0}|$ as given in FIGS. 8 and 9. FIG. 10 shows that within the entire processing interval $D<D_{EX}$ there is no transition from $R_1$ to $R_2$. $U_M$ has the voltage level of $U_{MO}$ over the overall feed distance. Apart from the missing of the tool 120 the behavior of the resistance measurement represented in FIG. 10 can also indicate the missing of the work piece 130.

Again referring to the exemplary method represented in FIG. 7, if it is determined at decision block 760 that the transition from $R_1$ to $R_3$ occurs in the distance interval $D<D_{EX}$ this shows that either the tool 120 or the work piece 130 are not correct. Possible reasons for such a situation could be: The tool 120 is too short or a wrong type of tool is available in the tool holder 114 of the spindle 110. A wrong work piece 130 is used or the correct work piece 130 is erroneously positioned. The defect is visualized to the user of the machine 100, 400 at step 765 via the display 646, and the method ends at step 770.

During normal operation it is determined at decision block 785 whether a change occurs from the resistance $R_2$ to $R_3$. If this is not the case, the processing of the work piece is finalized at block 787 and the method ends at step 789. When a change of the resistance $R_x$ from $R_2$ to $R_3$ is detected, it is indicated to the user at step 791 via the monitor 646 of the machine 100, 400 that the tool 120 and/or the work piece 130 are defective. At block 793 the monitoring system 642 stops the operation of the machine tool 100 and 400 via the control 644 by turning off the convertor 170, and the method ends at step 795.

Thus, the inventive method enables a cost-effective monitoring of the operation of a machine tool without impairing its processing time and thus without impairing its throughput.

The invention claimed is:

1. An apparatus for monitoring the operation of an electrically conductive tool of a machine tool, comprising:
  a. at least one electrically conductive spindle for holding the tool;
  b. a detector which is configured to determine an electrical resistance between the spindle and an electrically conductive work piece to be processed;
  c. wherein the spindle is electrically isolated from the machine tool or the apparatus is adapted to electrically isolate the work piece to be processed from the machine tool; and
  d. a voltage divider, wherein the voltage divider comprises at least two resistances, wherein a center tap of the voltage divider is conductively connected with the spindle and the detector, and wherein one end of the voltage divider is conductively connected with the work piece.

2. The apparatus according claim 1, wherein the detector is operable to generate an alarm.

3. The apparatus according to claim 1, wherein the work piece is ranged on an electrically conductive work bench of the machine tool and the detector is conductively connected with the work bench.

4. The apparatus according to claim 1, wherein the work piece is arranged on an electrically isolating work bench of the machine tool.

5. The apparatus according to claim 1, wherein the electrically conductive work bench is electrically isolated from the machine tool and the detector is conductively connected with one of:
  1) the electrically conductive work piece to be processed; or
  2) with the electrically conductive work bench which is electrically isolated from the machine tool.

6. The apparatus according to claim 1, further comprising a work piece clamping device which is adapted to clamp the work piece in such a way that it is electrically isolated from the machine tool.

7. The apparatus according to claim 1, wherein the detector comprises one of:
  1) a current meter and a voltage source; or
  2) a voltage source or a current source and a voltage detector.

8. The apparatus according claim 1, wherein the detector is configured to detect that the spindle, the tool and the work piece:
  lead to a first electrical resistance if the tool is not in contact with the work piece, or if there is no tool or no work piece available,
  lead to a second electrical resistance if the tool is in contact with the work piece, or lead to a third electrical resistance if the tool is in contact with the work piece and the tool or the work piece are defective.

9. The apparatus according to claim 8, wherein the detector is further configured to detect:
   a. that there is an incorrect tool or an incorrect work piece if a transition from the first electrical resistance to the second electrical resistance is found at a distance between the spindle and the work piece which is larger than predetermined distance or
   b. that there is a correct operation of the machine tool if the transition from the first electrical resistance to the second electrical resistance is found within a predetermined distance interval between the spindle and the work piece or
   c. that the tool is missing if no transition is found from the first electrical resistance to the second electrical resistance within a predetermined distance interval between the spindle and the work piece or
   d. that there is an incorrect tool or an incorrect work piece if a transition from the first electrical resistance to the second electrical resistance is found at a distance between the spindle and the work piece which is smaller than a predetermined distance.

10. The apparatus according to claim 9, wherein the detector is further configured to determine that there is an incorrect tool or an incorrect work piece if a transition is found from the second electrical resistance to the third electrical resistance.

11. The method according to claim 9, wherein the detector is configured to monitor that the behavior of the electrical resistance essentially follows a predetermined behavior when processing the work piece.

12. The apparatus according to claim 11, wherein the behavior of the electrical resistance is below a first predetermined envelope and above a second predetermined envelope or is within predetermined area threshold values when processing the work piece.

13. The apparatus according to claim 1, wherein the detector is connected to a monitoring system of the machine tool, and wherein the monitoring system is configured to interrupt the operation of the machine tool.

14. A method for monitoring a machine tool having an electrically conductive spindle when processing an electrically conductive work piece, wherein the spindle holds an electrically conductive tool, and wherein the spindle or the work piece is electrically isolated from the machine tool, the machine tool further comprising a voltage divider, wherein the voltage divider comprises at least two resistances, wherein a center tap of the voltage divider is conductively connected with the spindle and a detector, and wherein one end of the voltage divider is conductively connected with the work piece, the method comprising:
   determining a variation of the electrical resistance between the spindle and the work piece with the detector.

15. A method for monitoring a machine tool having an electrically conductive spindle when processing an electrically conductive work piece, wherein the spindle holds an electrically conductive tool, and wherein the spindle or the work piece is electrically isolated from the machine tool, the machine tool further comprising a voltage divider, wherein the voltage divider comprises at least two resistances, wherein a center tap of the voltage divider is conductively connected with the spindle and a detector, and wherein one end of the voltage divider is conductively connected with the work piece, the method comprising:
   determining a variation of the electrical resistance between the spindle and the work piece with the detector; and
   using an apparatus according to claim 1.

* * * * *

UNITED STATES PATENT AND TRADEMARK OFFICE
CERTIFICATE OF CORRECTION

PATENT NO. : 9,079,280 B2  
APPLICATION NO. : 13/347177  
DATED : July 14, 2015  
INVENTOR(S) : Lange et al.

Page 1 of 1

It is certified that error appears in the above-identified patent and that said Letters Patent is hereby corrected as shown below:

In the Claims:

Column 14, line 37 (claim 3), please delete "ranged" and substitute --arranged--.

Signed and Sealed this  
Seventeenth Day of November, 2015

Michelle K. Lee  
*Director of the United States Patent and Trademark Office*